United States Patent [19]

Howell

[11] 4,002,070
[45] Jan. 11, 1977

[54] SAMPLE INJECTION SYSTEM

[75] Inventor: Gary W. Howell, Elkton, Md.

[73] Assignee: E. I. Du Pont de Nemours and Company, Wilmington, Del.

[22] Filed: Feb. 26, 1975

[21] Appl. No.: 553,427

[52] U.S. Cl. .......................... 73/422 GC; 137/565; 137/605

[51] Int. Cl.² ........................................ G01N 1/14

[58] Field of Search .... 73/422 R, 422 GC, 422 TC, 73/423 R; 137/563, 565, 604, 605; 222/133

[56] References Cited

UNITED STATES PATENTS

| | | | |
|---|---|---|---|
| 2,994,224 | 8/1961 | Brown | 73/422 R |
| 3,039,141 | 6/1962 | Bauer | 137/604 X |
| 3,186,234 | 6/1965 | Solnick et al. | 73/422 GC |
| 3,754,443 | 8/1973 | Harris | 73/422 GC |
| 3,940,994 | 3/1976 | Klee et al. | 73/422 GC |

Primary Examiner—Robert G. Nilson

[57] ABSTRACT

Disclosed herein is an apparatus for injecting a quantity of sample liquid into a continuously flowing carrier liquid comprising a housing, a primary channel, carrier inlet and outlet means both connected to the primary channel to form a carrier conduit through the housing, sample inlet and outlet channels both connected to the primary channel to form a sample conduit through the housing, a normally closed pressure relief valve disposed in the primary channel between the sample conduit and the carrier conduit, and means to change the pressure differential between the liquid flowing in the sample and carrier conduits.

7 Claims, 5 Drawing Figures

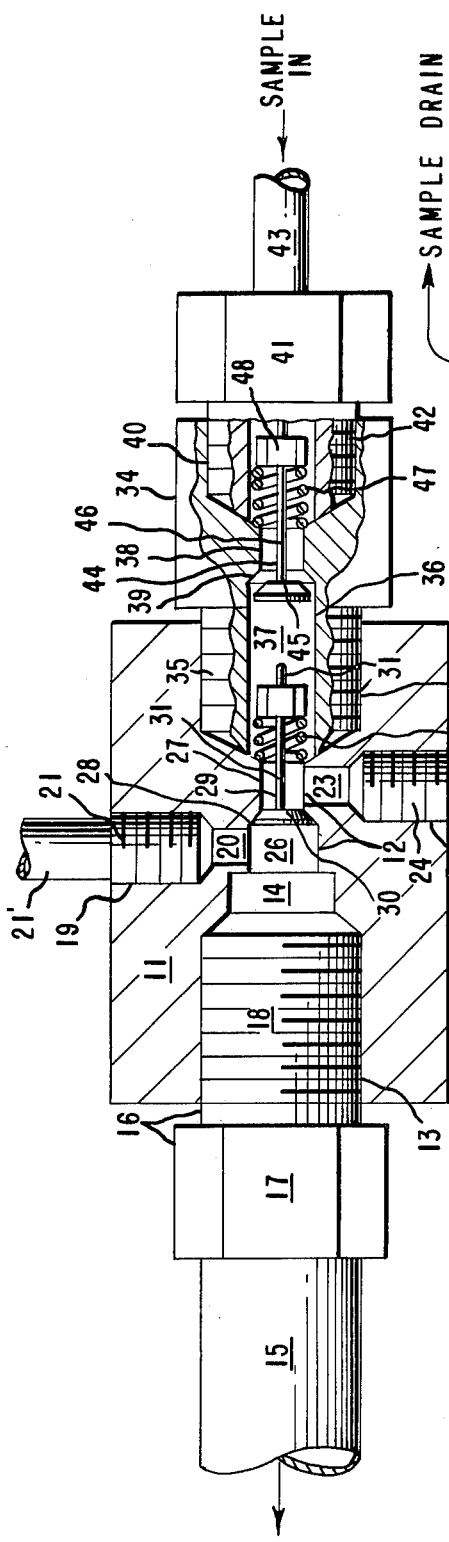

SAMPLE INJECTION SYSTEM

BACKGROUND OF THE INVENTION

1. Field of the Invention

The present invention relates to an apparatus for injecting a quantity of liquid sample into a continuously flowing carrier liquid. More particularly, it relates to an apparatus for repetitively injecting a predetermined discrete quantity of sample liquid into a continuously flowing carrier liquid. Such an apparatus is useful as a sample injection system for use with a liquid chromatographic column. In such use, the carrier liquid is referred to as the mobile phase.

2. Discussion of the Prior Art

Liquid chromatographs have traditionally been used as research tools. There is, however, a growing trend to use these instruments as industrial process monitors. In such use, the traditional, manual introduction of sample into the column by means of hypodermic injection through a septum is unacceptable.

Automatic injection systems for liquid chromatographs have been developed for process use. Normally, they consist of a "multi-way" valving system designed to isolate a "slug" of sample in a separate portion of the system, usually a short length of tube connected to one set of valves, and then to switch the valves so that the isolated slug of sample is introduced into the continuously flowing carrier stream. Such systems, however, have poor valve life and are prone to leakage. Furthermore, they require an interruption in the flow of carrier liquid, which causes a number of problems, both in the design of the injection system and in the "up-stream" operation of the carrier liquid system. There is, therefore, the need for a simple, reliable, accurate and durable sample injection system for use in liquid chromatographic applications, particularly one which will operate without interrupting the flow of carrier liquid.

SUMMARY OF THE INVENTION

This has been achieved by providing an apparatus for injecting a quantity of sample liquid into a continuously flowing carrier liquid comprising:

a. a primary housing having a primary channel therein;

b. a carrier inlet in the primary housing connected to the primary channel;

c. a carrier outlet in the primary housing connected to the primary channel adjacent to the carrier inlet, the carrier inlet and outlet together forming a carrier conduit through the primary housing;

d. a sample inlet in the primary housing connected to the primary channel;

e. a sample outlet in the primary housing connected to the primary channel adjacent to the sample inlet, the sample inlet and outlet together forming a sample conduit through the primary housing;

f. a primary pressure relief valve disposed within the primary housing in the primary channel between the sample conduit and carrier conduit, the primary pressure relief valve being biased to the normally closed position to prevent intermixing of liquid flowing in the sample conduit and liquid flowing in the carrier conduit; and g. means to change the pressure differential between the liquid flowing in the carrier conduit and the liquid flowing in the sample conduit to the point where the primary pressure relief valve opens to admit sample liquid into the carrier conduit.

In the preferred embodiment, the sample inlet comprises a sample inlet tube connected to the primary channel and containing a secondary pressure relief valve. The secondary pressure relief valve is biased to the normally closed position, as with the primary pressure relief valve. The force with which the primary pressure relief valve is biased closed is greater than or at least equal to the force with which the secondary pressure relief valve is biased closed. In a still more preferred embodiment, the primary and secondary channels comprise frustroconically-shaped regions and the pressure relief valves comprise conically-shaped pistons movably mounted in their respective channels and spring loaded into engagement with the frustroconically-shaped regions of the channels.

In an even more preferred embodiment, the means to change the pressure differential is a pumping system connected to the sample outlet. This system comprises a housing having a motor cylinder, first and second channels, and a sample drain orifice formed therein. The first channel is a cylindrical pump channel with its axis parallel to the axis of the pump cylinder. One end of the first channel is connected to the motor cylinder and the other end is connected to the sample outlet. One end of the second channel is connected to the first channel at a point adjacent to the connection of the first channel to the motor cylinder, and the other end of the second channel is connected to the sample drain orifice. The pumping system further comprises a piston movably mounted in the motor cylinder, a cylindrical rod carried by the piston and extending into the first channel, and means to seal the rod to the walls of the first channel in movable, leak-tight association. The end of the rod disposed within the first channel is normally positioned between the point at which the first channel is connected to the motor cylinder and the point at which the first channel is connected to the second channel. Some means to move the piston in the motor cylinder and thereby move the rod in the first channel is also provided. The use of such a pumping system in the sample injection system also improves the precision of the system, particularly with regard to the quantity of sample injected into the carrier stream.

BRIEF DESCRIPTION OF THE DRAWINGS

The present invention can best be described with reference to the following figures in which:

FIG. 1 is a side view, shown partially in cross section, of one embodiment of the present invention;

FIG. 2 is an enlargement of one portion of the embodiment of FIG. 1, showing the operation of the pressure relief valve in more detail;

DESCRIPTION OF THE PREFERRED EMBODIMENTS

Figure 3:
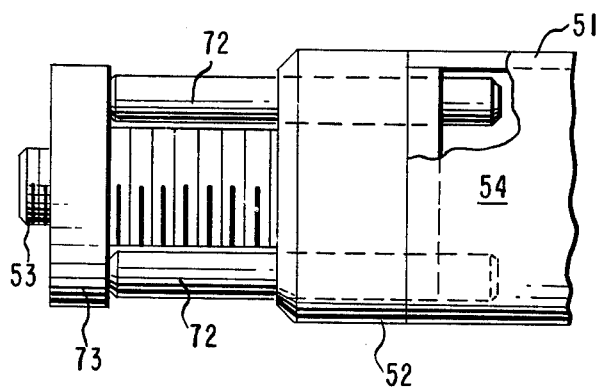
FIG. 3 is a top view of a portion of the pumping system of FIG. 1.

Referring to FIG. 1, primary housing 11 has formed in it a primary channel 12. In the embodiment illustrated, this primary channel is a complex channel composed of three portions: a first portion 26, a second portion 27, and a frustroconically shaped portion 28 connecting the first and second portions. Housing 11 also has formed in it a carrier outlet in the form of an internally threaded recess 13 and an enlarged channel 14 connecting the threaded recess 13 to the first portion 26 of channel 12.

A liquid chromatographic column 15 is connected to the carrier outlet by means of a fitting 16 which comprises a nut 17 with an externally threaded extension 18. Fitting 16 has an internal channel formed in it to connect the column to the primary channel through the carrier outlet. The column is connected to the fitting by some suitable method.

Also formed in the primary housing is a carrier inlet composed of an internally threaded recess 19 and a connecting channel 20 which connects threaded recess 19 to the first portion 26 of primary channel 12. Disposed in threaded recess 19 is a threaded fitting 21 which is connected to carrier liquid inlet line 21'. Threaded recess 19, connecting channel 20, the first portion 26 of primary channel 12, enlarged channel 14, and threaded recess 13 all combine to form a carrier conduit through the primary housing. The carrier liquid, or mobile phase as it is referred to in liquid chromatographic work, can then pass directly through the primary housing 11 into the liquid chromatographic column 15.

The primary housing also contains a sample outlet composed of a threaded recess 22 connected to the second portion 27 of primary channel 12 by a connecting channel 23. Disposed in threaded recess 22 is a threaded fitting 24 connected to a tube 24'. Also formed in the primary housing is a sample inlet which, in the embodiment shown, consists of an internally threaded recess 25 connected directly to the second portion 27 of primary channel 12. Threaded recess 25, second portion 27 of primary channel 12, connecting channel 23, and threaded recess 22 all combine to form a sample conduit running through the primary housing.

In the embodiment shown, primary channel 12 is divided into three portions; a first portion 26 to which both the carrier inlet and the carrier outlet are connected, a second portion 27 to which both the sample inlet and sample outlet are connected, and a frustroconically shaped portion 28 connecting the first and second portions. The first and second portions of the primary channel have concentric axes, but the diameter of the second portion is smaller than the diameter of the first portion.

Disposed in primary channel 12 is a primary pressure relief valve which comprises a piston 29 having a conically shaped portion 30 and a rod 31. Rod 31 is attached to the smaller end of the conically shaped portion of the piston, and the conically shaped portion of the piston engages the frustroconically shaped portion 28 of the primary channel. Piston 29 is spring loaded into engagement with the surface of the frustroconically shaped portion 28 of the primary channel by a spring 32 which fits around rod 31 and is compressed against the base of threaded inlet recess 25 by a nut 33 carried by the threaded end of rod 31. These features can best be seen by reference to the enlarged portion of FIG. 1 shown in FIG. 2.

The primary pressure relief valve is normally closed; i.e., the conically shaped portion of piston 29 tightly engages the frustroconically shaped portion of the primary channel. It is kept in its position by the tension in spring 32 and also by the pressure of the carrier liquid as it passes through the first portion 26 of primary channel 12. However, if the pressure of the sample liquid in the second portion 27 of the primary channel increases to the point where the force exerted on the back of the conically shaped portion 30 of the piston exceeds the forces tending to keep that conically shaped portion of the piston in engagement with the frustroconically shaped walls of portion 29, then piston 29 will move to the left and there will be a connection between the first and second portions of the primary channel. Sample liquid will be introduced into the carrier liquid, without stopping the flow of carrier liquid through the system. This situation is shown in FIG. 2. Normally, the pressure of the sample liquid in the second portion 27 of the primary channel 12 is not high enough to move the piston from its normally closed position. It is only when the pressure in this portion of the primary channel is increased that the piston moves. It is for this reason that the piston and its associated parts is referred to as a pressure relief valve.

The housing, fittings and valves used in the present invention are all made from any suitable material such as stainless steel, or even plastic if the conditions of use are right. Threaded fittings 21 and 24 are most conveniently Swagelok fittings.

To complete the apparatus, some means must be provided to change the pressure differential between the liquid flowing in the carrier conduit and the liquid flowing in the sample conduit to the point where the primary pressure relief valve opens. There are a number of ways in which this can be accomplished. One way is to insert a valve in the sample outlet line 24. When the valve is closed the pressure in channel 27 will increase, and, provided the spring constant of spring 32 and the pressure of the mobile phase are properly chosen, the pressure relief valve will open. If the valve in the sample outlet is designed to operate periodically, then the pressure relief valve will open and close periodically.

The system shown in FIG. 1 has been specially designed to yield a high degree of precision and reproducibility in the amount of sample injected into the chromatographic column. To accomplish this, a more sophisticated sample inlet is used.

In the embodiment shown, the sample inlet comprises a secondary housing 34 with a threaded extension 35 which engages threaded inlet recess 25 of the primary housing. The secondary housing 34 has within it a secondary channel 36 which is divided into a first section 37, a second section 38, and a frustroconically-shaped section 39 connecting the first and second sections. The secondary housing also has an enlarged threaded recess 40 which is connected to the second section 38 of the secondary channel. The first section 37 of the secondary channel is connected to the second portion 27 of primary channel 12. The second section of the secondary channel has an axis which is concentric with the axis of the first section, but it has a diameter smaller than that of the first section. The sample inlet further comprises a sample inlet tube 43 and a sample inlet fitting. In the embodiment illustrated, the sample inlet fitting comprises a nut 41 and a threaded extension 42 which fits into threaded recess 40.

Also included in the sample inlet is a secondary pressure relief valve which is similar in design to the primary pressure relief valve. It consists of a piston 44 with a conically shaped portion 45 attached to a rod 46.

The conically shaped portion of the piston is normally pressed into engagement with the frustroconically shaped section 39 of the secondary channel by a spring 47 which is held under tension against the base of inlet recess 40 by a nut 48 held by the threaded end of rod 46. This secondary pressure relief valve is virtually identical to the primary pressure relief valve. It is spring loaded so that it is normally in a closed mode. The tension of the spring used in the secondary pressure relief valve is such that the normal pressure of the sample flowing into the sample inlet is enough to displace the piston to the left and open the valve. It can be either less than or equal to the tension in the primary pressure relief valve. It can be equal to the tension in the primary relief valve because in the primary relief valve, there is carrier liquid back pressure on the left hand side of piston 29 to aid in biasing piston 29 to the normally closed position.

The choice of proper spring material and construction to obtain the proper tension is important, but the choice is within the skill of one normally skilled in the art. The dimensions of the primary and secondary housings and the connecting fittings are not critical. It is preferable, however, to keep the volume of the region between piston 29 and piston 44 to a minimum. This increases the resolution of the system by decreasing the "dead-volume" in the system. Resolution, in this context, means the ability to resolve difference in composition between two closely spaced portions of the sample stream. Maintaining a small dead-volume also increases the precision of the system by making it easier to clean. Between each aliquot introduced into the column, the entire sample conduit is flushed by the continually changing flow of sample through the sample conduit.

The system illustrated in FIG. 1 further comprises a pumping system, generally indicated by 80, which consists of a pump and a motor to drive the pump. The system consists of a housing 50 which, in the embodiment shown, comprises a cylinder 51, a cap 52, and externally threaded cylindrical member 53. Formed in the housing is a motor 54. The pump comprises a first channel 55, with an axis parallel to the axis of the motor cylinder; and a second channel 56. The first channel functions as a pump cylinder. One end of the first channel 55 is connected to the motor cylinder, and the other end is connected to tube 24' leading to the sample outlet. Tube 24' has a threaded end which fits in threaded recess 71 of cylindrical member 53. Alternately, a Swagelok fitting can be used. Second channel 56 provides a connection between the first channel 55 and a sample drain orifice located on the surface of the housing. In the embodiment illustrated, the sample drain orifice is in the form of a threaded recess 57 which houses a threaded drain fitting 58 and a connecting line 59. Fitting 58 may also be a Swagelok fitting.

A resistance, possibly in the form of a valve or a restriction 88 in the sample drain line 59, to raise the internal pressure in the drain line above atmospheric pressure during flow conditions has been found to be helpful in increasing the precision of the system. This resistance aids in hydraulically closing the secondary pressure relief valve.

Located inside motor cylinder 54 is a motor piston 60 which carries with it a cylindrical rod 61. This rod extends into the first channel. In its normal position, the end of rod 61 which is disposed within the first channel is located between the point at which the first channel is connected to the motor cylinder and the point at which the first channel is connected to the second channel.

Figure 4:
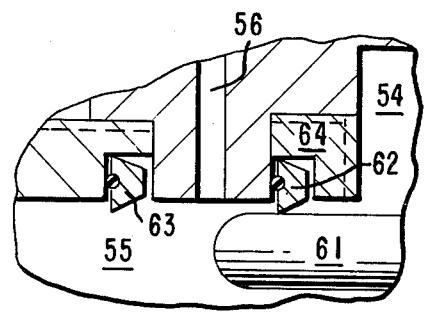
FIG. 4 is an enlargement of one portion of the pumping system of FIG. 1.

As can be seen from FIGS. 1 and 4, rod 61 is held in leak-tight association with the walls of the first channel 55 by two gaskets 62 and 63. In the embodiment shown, these gaskets are commercially available seals. Seal 62 is held in place by threaded retainer 64 which fits in threaded recess 65 of cap 52. Seal 63 is held in place by externally threaded cylindrical member 53 which fits into threaded recess 66 in cap 52.

In the embodiment illustrated, piston 60 is moved pneumatically. Motor cylinder 51 terminates in a cap 67 containing a channel 68 with a threaded recess 69. A threaded tube 70 connects the motor cylinder 54 to a source of air through channel 68. Air at 60 psi applied to the motor cylinder, behind piston 60, by tube 70 will force the piston to the left. This will drive rod 61 further into first channel 55. Any suitable alternative means, such as a solenoid, can be used as the means to move piston 60.

Also included in the pumping system is a stop which in the embodiment shown consists of a pair of rods 72 which slip through channels formed in cap 52, and extend into motor cylinder 54. A threaded collar 73, which engages externally threaded member 53, is used to position the rods within the motor cylinder. Rods 72 act as stops to prevent piston 60 from moving any further to the left. By adjusting the position of these rods, the distance that rod 61 will move into the first channel 55 can be controlled. This can best be seen by reference to FIG. 4.

Some means to control the air being supplied to the motor cylinder from the source of air should also be provided. In the embodiment illustrated, this consists of a solenoid valve 74. By periodically activating this valve, piston 60 can periodically be driven to the left. Air may also be applied to the other end of piston 60 through threaded recess 75 and channel 76 formed in cap 52. A threaded fitting 77, which may be a Swagelok fitting, connects recess 75 to a source of air, through valve 78. The same source of air supplied to tube 70 may be used if a switching valve is supplied.

In normal operation, carrier liquid enters tube 21' and passes directly through the interconnecting channel to the column 15. Sample liquid similarly enters tube 43, under sufficient pressure to move piston 44, passes into the connecting portions of the primary and secondary channels through tube 24 and out the tube to a drain through first channel 55, second channel 56, and tube 59. The system remains in this condition, with the first pressure relief valve, represented by piston 29, in a closed position, the second pressure relief valve, represented by piston 44, in an opened position, and piston 60 positioned so that the end of rod 61 residing in the first channel 55 is disposed between the connection of the first channel to the second channel and the connection of the first channel to the pump cylinder. When valve 74 is activated, however, air enters pump cylinder 54 behind piston 60 and drives it to the left. The piston carries rod 61 with it, so, as the piston moves, rod 61 begins its travel into the first channel 55. As it passes the connection between first channel 55 and second channel 56, it acts as a valve to close off the path of the sample fluid out of the system to the sample drain. As this happens, no further sample fluid can enter the system. As a result of this, the force tending to displace piston 44 to the left dissipates, and the valve closes under the action of spring 47. This seals the samples in the region of the system between the conical portion of piston 44 and the end of rod 61 as it sits in first channel 55.

Since air is still supplied to the back of piston 60, rod 61 continues to advance into first channel 55. As the rod advances, it increases the pressure in the now sealed sample containing region between piston 44 and rod 61 to the point where the force exerted on the back of the conically-shaped section of first piston 29 exceeds that necessary to move the piston to the left. As this occurs, piston 29 is moved to the left and sample flows from the sealed sample containing region into the carrier outlet where it mixes with the carrier liquid and flows into the column.

Rod 61 continues its advance until piston 60 contacts the ends of rods 72 and stops. Rod 61, therefore, advances into first channel 55 a specified predetermined distance. Because of its motion, a specified volume of sample is displaced into the carrier liquid. When rod 61 ceases its advance, the pressure in the sample conduit equilibrates, and the pressure of the mobile phase act to close the primary relief valve by forcing piston 29 back into engagement with the frustroconically shaped portion of the primary channel.

Valve 74 is closed, and valve 78 is opened to force piston 60 to return to its initial position. A path for the sample liquid to pass to the sample drain is reestablished, and sample again flows continuously through the system.

Figure 5:
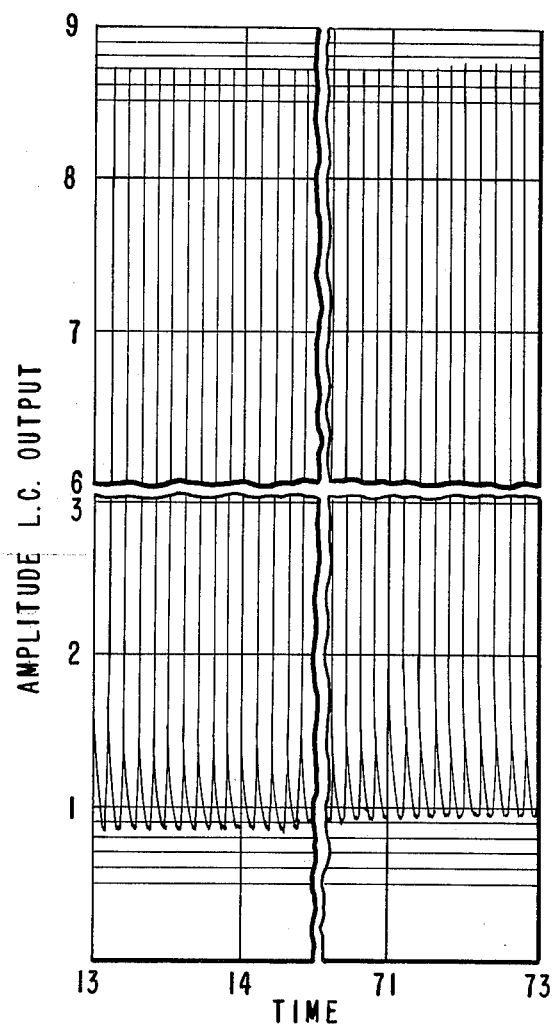
FIG. 5 is a plot of the output of a liquid chromatograph as a function of time showing the precision and accuracy of the injection system shown in FIGS. 1 and 2.

FIG. 5 shows the output of a liquid chromatograph as a function of time. The chromatograph used was a Du Pont 841 Liquid Chromatograph. The sample was a 0.1% solution of acetone in water and the mobile phase was water at 3000 psi. The duration of the sample injection was 1 second, or a volume of 80 $\mu$l, and sample injection cycle was one injection per minute. The break in the plot is equivalent to about 9 hours. As can be seen from the plot, the results are highly reproducible over a long time.

The above description is intended to exemplify only one embodiment of the present invention. A number of modifications apparent to one skilled in the art can be made to the present invention. For example, any suitable check valve can be used in place of the pressure relief valves disclosed. Such modifications are intended as part of the present invention as described in the following claims.

What is claimed is:

1. An apparatus for injecting a quantity of a sample liquid into a continuously flowing carrier liquid, comprising:
   a. a primary housing having a primary channel therein;
   b. a carrier outlet in said primary housing connected to said primary channel;
   c. a carrier inlet in said primary housing connected to said primary channel adjacent to said carrier outlet, said carrier inlet and outlet together forming a carrier conduit through said primary housing;
   d. a sample outlet in said primary housing connected to said primary channel;
   e. a sample inlet in said primary housing connected to said primary channel adjacent to said sample outlet, said sample inlet and outlet together forming a sample conduit through said primary housing;
   f. a primary pressure relief valve disposed within said primary housing in said primary channel between said sample conduit and said carrier conduit, said primary pressure relief valve being biased to the normally closed position to prevent intermixing of liquid flowing in said sample conduit and the liquid flowing in said carrier conduit; and
   g. means to change the pressure differential between the liquid flowing in said carrier conduit and the liquid flowing in said sample conduit to the point where the primary pressure relief valve opens to admit sample liquid into said carrier conduit, said means comprising
      i. a pumping system comprising a housing, and a motor cylinder, first and second channels, and a sample drain orifice all formed in said housing, said first channel being a cylindrical pump channel with an axis parallel to the axis of said motor cylinder, one end of said pump channel being connected to said motor cylinder and the other end being connected to said sample outlet, one end of said second channel being connected to said pump channel at a point adjacent to the connection of said first channel to said motor cylinder and the other end of said second channel being connected to said sample drain orifice, said first and second channels forming a continuous path from said sample outlet to said sample drain orifice;
      ii. a piston movably mounted in said motor cylinder;
      iii. a cylindrical rod carried by said piston and extending into said first channel;
      iv. means to seal said cylindrical rod to the walls of said first channel in movable, leak-tight association, the end of said rod disposed within said first channel being normally positioned between the point at which said first channel is connected to said motor cylinder and the point at which said first channel is connected to said second channel; and
      v. means to move said piston in said motor cylinder and thereby move said rod in said first channel.

2. The apparatus of claim 1 wherein said sample inlet comprises a secondary pressure relief valve connected to said primary channel and a sample inlet tube connected to said secondary pressure relief valve, said secondary pressure relief valve being biased to the normally closed position, the force with which said primary pressure relief valve is biased closed being greater or equal to the force with which said secondary pressure relief valve is biased closed.

3. The apparatus of claim 1 wherein said sample inlet comprises:
   a. a sample inlet tube;
   b. a secondary housing connected to said primary housing and having a secondary channel running through it, said secondary channel being formed from a first section connected to the primary channel in said primary housing, a second section connected to said sample inlet tube, and a frustroconically shaped section connecting said first and second section, said second section having an axis concentric with the axis of said first section and a diameter smaller than the diameter of said first section; and
   c. a conically shaped piston movably mounted in said secondary channel, said piston being spring loaded into engagement with the frustroconically shaped section of said secondary channel.

4. The apparatus of claim 3 wherein:
a. said primary channel comprises a first portion to which said carrier inlet and outlet are connected and a second portion to which said sample inlet and outlet are connected, and a frustroconically shaped portion connecting the first and second portions, said second portion having an axis concentric with the axis of said first portion and a diameter smaller than the diameter of said first portion; and
b. said primary pressure relief valve comprises a conically shaped piston movably mounted in said primary channel, said piston being spring loaded into engagement with the frustroconically shaped portion of said primary channel.

5. The apparatus of claim 1 wherein said pumping valve further comprises a stop to limit the extent to which said rod enters said first channel.

6. The apparatus of claim 5 wherein said means to move said piston is a source of pressurized air connected to said pump cylinder behind said piston.

7. The apparatus of claim 6 wherein said means to move said piston further comprises a normally closed valve connected between said source of pressurized air and said pump cylinder, and means to periodically activate said valve.

* * * * *